United States Patent
Freiin von Kapri et al.

(10) Patent No.: US 11,106,279 B2
(45) Date of Patent: Aug. 31, 2021

(54) EYE TRACKING CALIBRATION FOR A SURGICAL ROBOTIC SYSTEM

(71) Applicant: Verb Surgical Inc., Mountain View, CA (US)

(72) Inventors: Anette Lia Freiin von Kapri, Mountain View, CA (US); Denise Miller, Scotts Valley, CA (US); Joan Savall, Palo Alto, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 76 days.

(21) Appl. No.: 16/449,170

(22) Filed: Jun. 21, 2019

(65) Prior Publication Data
US 2020/0401219 A1    Dec. 24, 2020

(51) Int. Cl.
| | |
|---|---|
| *A61B 34/00* | (2016.01) |
| *A61B 34/30* | (2016.01) |
| *G06F 3/01* | (2006.01) |
| *A61B 17/00* | (2006.01) |
| *G06K 9/00* | (2006.01) |

(52) U.S. Cl.
CPC .............. *G06F 3/013* (2013.01); *A61B 34/25* (2016.02); *A61B 34/30* (2016.02); *A61B 2017/00216* (2013.01); *G06K 9/00604* (2013.01)

(58) Field of Classification Search
None
See application file for complete search history.

(56) References Cited

U.S. PATENT DOCUMENTS

| | | | |
|---|---|---|---|
| 8,793,620 B2 * | 7/2014 | Stafford | G06F 3/013 715/862 |
| 9,851,791 B2 | 12/2017 | San Agustin Lopez et al. | |
| 2006/0110008 A1 | 5/2006 | Vertegaal et al. | |
| 2013/0107207 A1 * | 5/2013 | Zhao | G06K 9/00604 351/206 |

(Continued)

OTHER PUBLICATIONS

International Search Report and Written Opinion for International Application No. PCT/US2019/039044, dated Apr. 8, 2020, 10 pages.

(Continued)

*Primary Examiner* — Kent W Chang
*Assistant Examiner* — Benjamin Morales
(74) *Attorney, Agent, or Firm* — Womble Bond Dickinson (US) LLP

(57) ABSTRACT

A method for passively calibrating and verifying eye tracking in a surgical robotic system. The gaze of a user facing a user display of a user console of a surgical robotic system is tracked while the user is using a user interface device (UID). When a user interaction to the UID is detected, an expected gaze position on the display of the user console is determined without instructing the user to look at the expected gaze position. The latter becomes a reference gaze point of the user at the time of detected user action. The measured gaze point of the user is compared with an acceptable threshold of the reference gaze point, and in response to a determination of a mismatch, calibration parameters used by the tracking are adjusted according to the reference gaze point. Other aspects are also described and claimed.

19 Claims, 3 Drawing Sheets

(56) References Cited

U.S. PATENT DOCUMENTS

| | | | |
|---|---|---|---|
| 2014/0160004 A1* | 6/2014 | Katz | G06F 3/04842 |
| | | | 345/156 |
| 2014/0282196 A1 | 9/2014 | Zhao et al. | |
| 2016/0314711 A1* | 10/2016 | Grubbs | A61B 90/361 |
| 2017/0180720 A1* | 6/2017 | Jarc | H04N 13/239 |
| 2018/0059782 A1 | 3/2018 | Lopez et al. | |
| 2019/0094963 A1* | 3/2019 | Nijs | G09G 5/37 |

OTHER PUBLICATIONS

Van Casteren, Maarten, "Setting Up Eye Tracker", MRC CBU Wiki, Jun. 6, 2013, retrieved from the Internet <http://lsr-wiki-01.mrc-cbu.cam.ac.uk/meg/SettingUpEyeTracker>.

* cited by examiner

EYE TRACKING CALIBRATION FOR A SURGICAL ROBOTIC SYSTEM

Aspects of the disclosure here relates to eye tracking and eye tracking calibration and verification techniques suitable for a surgical robotic system. Other aspects are also described.

BACKGROUND

Computer-assisted and robotic surgery systems allow healthcare practitioners to achieve greater accuracy, automation and/or less-invasive approaches while performing a variety of diagnostic and/or therapeutic procedures. Such technologies are broadly applicable to a variety of medical specialties, ranging from ophthalmology and anesthesiology, to orthopedics and interventional radiology. In robotic or robotic-assisted surgery, at least some of the introduced instruments may be attached to one or more robotic arms operated remotely (e.g., in tele-operation) by a user (e.g., surgeon). Different aspects of the robotic surgery system may use elements of eye tracking. Thus, it is desirable to determine the fitness of the calibration of the eye tracking, without pausing the on-going surgery.

SUMMARY

A method for eye tracking in a surgical robotic system that may be less intrusive (requires fewer additional steps within the setup procedure or workflow of the system to perform eye tracking calibration and verification operations) thereby reducing setup time of the system. In one aspect, eye tracking validation or verification is integrated within a setup process of the system or at any other time of operation of the system, without requiring a separate, active calibration routine.

In one aspect, the gaze of a user facing a user display of a user console of a surgical robotic system is tracked, while the user is using a user interface device (UID). When a user interaction with the UID is detected, an expected gaze position on the display of the user console is determined based on the detected user interaction. That becomes a reference gaze point for the user (at the time of the detected user interaction.) A measured gaze point of the user at that time is compared with the reference gaze point, to determine if they are within an acceptable difference threshold of each other. In response to determining a mismatch (they are not within the acceptable difference threshold), the algorithm used for tracking the user gaze (which is a process for determining the measured user gaze) is adjusted, e.g., one or more calibration parameters of the eye tracking algorithm that are responsible for producing the measured gaze point are adjusted. But if the measured gaze point is within the acceptable threshold of the reference gaze point, then tracking the gaze of the user continues without performing an eye tracking calibration method or without adjusting the calibration parameters.

The measured user gaze point may be determined by the tracking algorithm, based on a selected profile (selected from several available or stored profiles.) Each profile contains several gaze tracking calibration parameters, one or more of which may be used by the tracking algorithm. A profile may or may not be associated with a particular individual or person.

A profile may be associated with a particular usage scenario. For instance, there can be one profile that should be used when the user is wearing eye glasses, another that should be used when the user is wearing contact lenses, and still another that should be used when the user is wearing no corrective lenses on the eyes. There may be at least two different profiles that are associated with different lighting conditions (of the scene being captured by the user camera 118.) There may be at least two different profiles that are associated with different relative positions of the user to the user camera 118.

If the difference between the measured gaze point and the reference gaze point is outside of a first threshold and inside of second threshold, then a better matching measured gaze point needs to be calculated by the tracking algorithm, using a different or adjusted set of calibration parameters. The different or adjusted set of calibration parameters may have been previously stored, in one of several calibration profiles. A profile is selected, or the tracking parameters are adjusted, so that the eye tracking algorithm can use them to produce a new measured gaze point (e.g., from the current image data that captured the user's face) that should be at the reference gaze (i.e., within some acceptable threshold of the reference gaze.) In this manner, the need for an active calibration of the eye tracking algorithm (where the user is instructed to sequentially look at several, designated target points all over the view screen) is avoided.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Several aspects of the disclosure with reference to the appended drawings are now explained. Whenever the shapes, relative positions and other aspects of the parts described are not explicitly defined, the scope of the invention is not limited only to the parts shown, which are meant merely for the purpose of illustration. Also, while numerous details are set forth, it is understood that some aspects of the disclosure may be practiced without these details. In other instances, well-known circuits, structures, and techniques have not been shown in detail so as not to obscure the understanding of this description.

Figure 1:
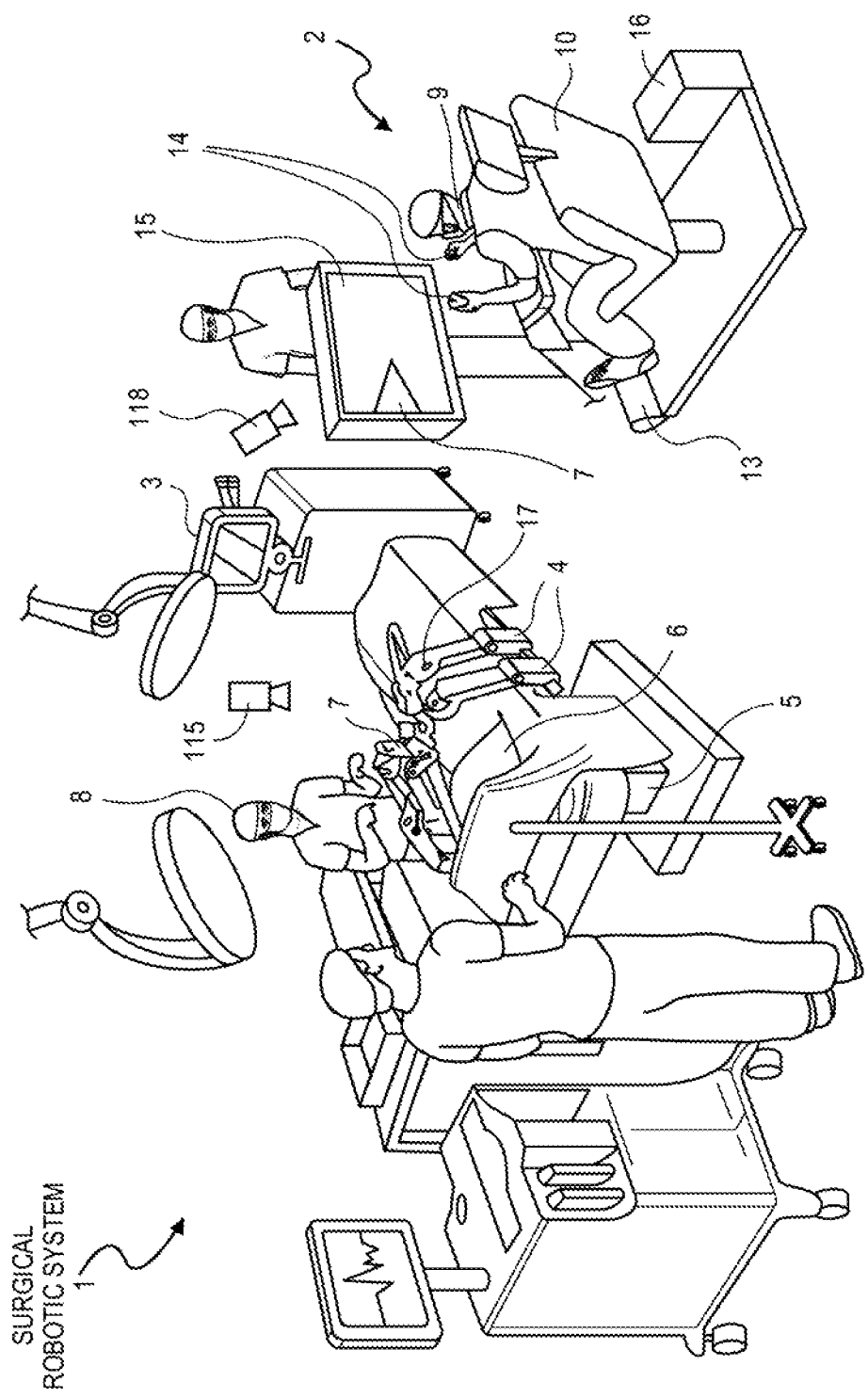
FIG. 1 depicts an example operating room arrangement with a surgical robotic system and remote operator.

Referring to FIG. 1, this is a pictorial view of an example surgical robotic system 1 in an operating arena. The robotic system 1 includes a user console 2, a control tower 3, an endoscope camera 115 that may or may not be at least partially inside the body of a patient 6, and one or more surgical robotic arms 4, at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of the arm 4, for executing a surgical procedure.

Each surgical tool 7 may be manipulated or actuated manually, robotically, or both, during the surgery. For example, the surgical tool 7 may be a tool used to enter, view, or manipulate an internal anatomy of the patient 6. For example, the surgical tool 7 may be, and is not limited to, at least one of a grasper that can grasp tissue of the patient, a scalpel that can make incisions in the tissue of a patient, a laser that can direct energy at a desired location on the patient, a hypodermic needle, and any specially designed tool or device for performing specific actions or carrying out desired effects during a surgery or operation. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator or user, may use the user console 2 to remotely manipulate or actuate the arms 4 and/or the attached surgical tools 7, e.g., teleoperation mode. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, a user camera 118, and at least one user display 15 that is configured to display, for example, a video feed from the endoscope camera 115. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to remotely control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate or actuate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, which opens or closes jaws of the grasper at a distal end of surgical tool 7 to grip tissue within patient 6. In one instance, the manipulation of the UID 14 may be directed toward positioning an action point of the arm 14, wherein the action point is the part of the arm 4 and/or surgical tool 7 that interfaces with the patient 6 at the surgical site. In one example, the surgical tool 7 may be a scalpel attachment that allows a user to make precise incisions, wherein the action point is the edge of the scalpel used to make the incisions. As another example of the action point being at an end effector, the action point may be a jaw of a grasper.

In some aspects, the communication between the platform 5 and the user console 2 may be through a control tower 3, which may translate user commands that are received from the user console 2 (and more particularly from the console computer system 16) into robotic control commands that transmitted to the arms 4 on the platform 5. The control tower 3 may also transmit status and feedback from the platform 5 back to the user console 2. The communication connections between the platform 5, the user console 2, and the control tower 3 may be via wired and/or wireless links, using any suitable ones of a variety of data communication protocols. Any wired connections may be optionally built into the floor and/or walls or ceiling of the operating room. The endoscope camera 115 may provide video output to one or more displays, including displays within the operating room as well as remote displays that are accessible via the Internet or other networks. The video output or feed may also be encrypted to ensure privacy and all or portions of the video output may be saved to a server or electronic healthcare record system. The endoscope camera 115 may be located outside of the patient body surgical site as shown in FIG. 1, or it may be positioned inside of the surgical site. For instance, the endoscope camera 115 may be connected to a surgical robot arm 4 such that it may provide a view of the surgical site inside the patient 6. The endoscope camera 115 may include multiple cameras, wherein a first endoscope camera may be located outside of the surgical site (which may be inside the body of the patient 6) and a second endoscope camera may be placed in the surgical site (e.g., inside the body of the patient 6.)

Figure 2:
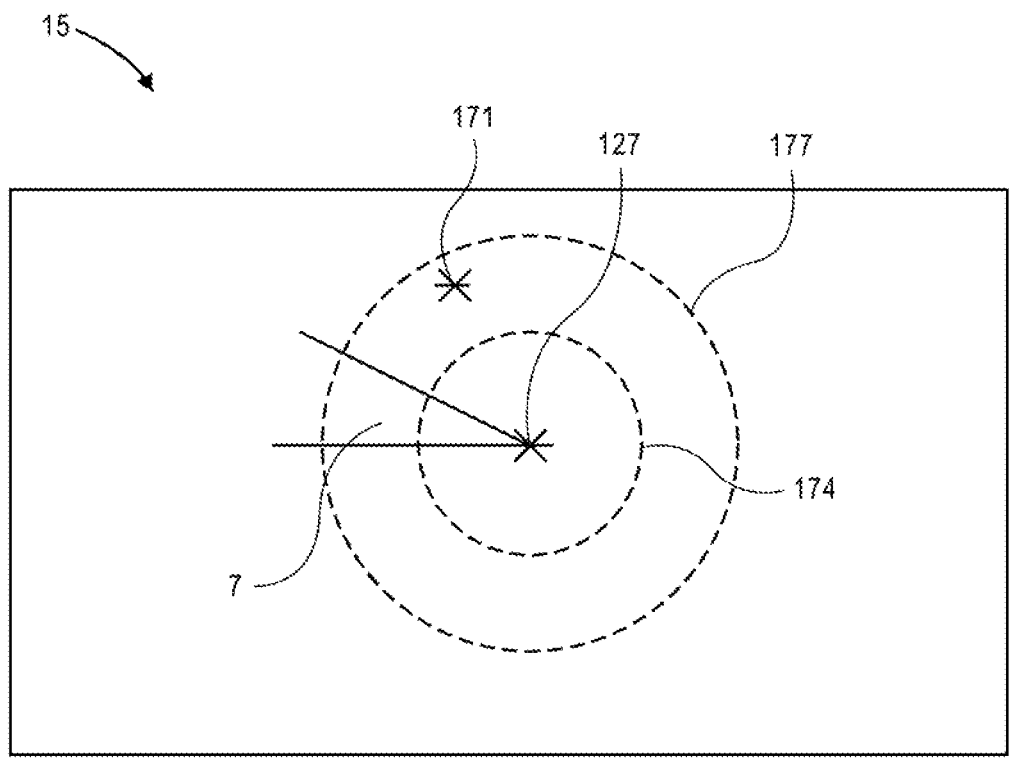
FIG. 2 demonstrates an example user display for a surgical robotic system.

The user camera 118 is used to track the gaze of the remote operator 9. The user camera 118 may include a photographic sensor and a light source. The light source may be any that can cast directional light on an eye of the remote operator 9, such as a light emitting diode (LED) based lamp, or a near-infrared projector. The photographic sensor takes sufficiently high frame rate images of an eye of the remote operator 9 to determine (measure) the gaze. FIG. 2 shows several regions on the user display 15 at which the gaze of the remote operator 9 could fall. The view screen of the display 15 in FIG. 2 shows the tool 7 having an action point 127 at its tip, surrounded by a first threshold region (first threshold 174), and further surrounded by a second threshold region (second threshold 177.) A measured gaze point 171 (determined by an eye tracking process as described below) is marked, that is outside of the first threshold 174 but inside the second threshold 177.

Eye Tracking Calibration and Verification

In a conventional eye tracking calibration process, a user is asked or instructed to look at certain target points which are displayed on the view screen and that span the entire screen area. The process executes an eye tracking algorithm that computes a measurement gaze point based on calibration parameters that are associated with the user (and based on image data of the user's face), when the user is looking at a respective target point. The parameters are then adjusted for the specific user based on feedback from the results of a comparison between the measurement gaze points and the target points, until the measurement gaze point match the target points. This calibration step, which produces the adjusted calibration parameters that are specific to the user, can last thirty seconds to a few minutes and requires the user's full attention. It therefore interferes with the setup workflow of the system, and creates an unwanted step in the setup of the system. As described below, an aspect of the disclosure here is a process that "passively" verifies or validates the user's tracked gaze, and then only if needed adjusts the calibration parameters that were being used to compute the tracked gaze, in a way that the user would not notice, or in a manner that is transparent to the user (e.g. taking place in the background.)

There are a few situations where one can infer that the user is looking at a specific location on the view screen user display 15 (without having to instruct or ask the user to do so.) In those situations, verification operations can be performed to verify that the tracked measured gaze point and the specific screen location which has been inferred, match one another. If they do not, then the calibration parameters used to track or measure the gaze point need to be adjusted (e.g., replace them with a different set of previously defined calibration parameters.), so that a new, measured gaze point (new in the sense that it is computed using the adjusted calibration parameters) is determined that matches the inferred screen location.

The term "match" as used here does not mean exactly equal but rather is within an acceptable threshold.

To infer that a user is looking at a specific screen location, at least the following four items may be considered:

1) A known, on-screen position of a given visual element at which the user is expected to be looking (without actually instructing the user to look at that location);

2) How the measured (calculated) gaze changes over time, before and after the visual element appears on screen (e.g., sudden jumps in the measured gaze);

3) The vicinity of the measured gaze point to the visual element on screen (e.g., without having been calibrated); and 4) The action that the user is performing (e.g., interacting with a particular GUI element such as a mouse cursor and mouse click selection, interacting with a handheld UID).

Situations in which one can infer where on the view screen the user is looking (without instructing the user to do so) include but are not limited to:

a) User login, during which one can infer that the user is looking at a known or predefined GUI element that in effect prompts the user to for example select or type in their name or user ID; the calculated gaze point at the moment in which the user is entering their name or password, and the known screen position of the user id dialog box or password dialog box, can be used as input to the verification operations;

b) User is interacting with GUI elements but the system is not in teleoperation mode; here, the GUI elements can include sliders, buttons, etc. In a general case, the GUI element may be the mouse pointer and its position when the user has clicked the mouse button, where it can be assumed that the user is looking at the mouse pointer when they are selecting something on screen; in that case, the mouse pointer position at the time of the mouse click, and the calculated gaze point at that moment, are input to the verification operations.

c) GUI elements that pop-up during teleoperation mode, such as notifications with icons or other reference images; if a notification pops-up on screen and the measured gaze point moves to a location close to where the notification appears on screen, then one can infer that the user is looking at that notification. The location of the notification when it appears on screen (together with the measured gaze point at that moment) may be used as input to the verification operations.

d) Tool tips during teleoperation mode, when the corresponding UID has been manipulated; for example, the system detects that during teleoperation mode, a UID grasper is being squeezed, which is translated by the system into the jaws of a corresponding grasper tool closing; at that point, one can infer that the user is looking at the tool jaws which should be on-screen. In that case, the 2D screen location of the tool jaw is determined using transformation techniques. The determined 2D screen location and the measured gaze point at that moment are then verified. Note here that the 2D screen location of the tool tip may be calculated by using the transformation matrices of the tool tip and the endoscope to calculate the transformation matrix of the tooltip in relation to the endoscope transformation, which enables the calculation of the pixel position of the tool tip by looking at the intrinsic parameters of the endoscope camera and transforming them into pixel space.

Thus, as explained above, the tracking verification and calibration parameter adjustment method is integrated within the "normal" workflow of setting up a surgical robotic system, without requiring a typical active calibration step where the user is instructed to look at various locations across the entire view screen.

Eye Tracking Verification

Upon completion of a calibration method, it is typical to validate the adjusted calibration parameters, by performing an eye tracking verification process. In an example conventional verification process, the user is presented with a target point on screen (at a known location on the user display 15) and is asked to look at that point (similar to what is done in a convention calibration process.) The calculated gaze point (calculated using the adjusted calibration parameters) at that moment is then compared to the presented target point's location; if these two are different by at least a threshold amount, the calibration process is repeated. For the eye tracking verification process, one can use the same situations as for the eye tracking calibration described above. What needs to be inferred is the location on screen at which the user is looking. That inferred location is then compared with the calculated gaze point to perform the verification step.

Automatically Changing a Calibration Profile

Another aspect of the disclosure here that may result in more efficient calibration of eye tracking in a surgical robotic system is the automatic changing of the calibration parameters. There may be different sets of calibration parameters (referred to here as profiles) defined and stored and associated with one user, where each set or profile is associated with a different configuration of the user console 2, respectively. For example, there may be several configurations of the user console 2 each of which has a different combination of view screen tilt and distance between the seat 10 (on which the remote operator or user sits during teleoperation) and the view screen (user display 15.) The appropriate set of calibration parameters can be automatically loaded (into the calibration method) whenever the user changes the configuration of the user console 2. Thus, in response to detecting a new configuration of the user console 2, the process determines whether or not to select a different set of calibration parameters (that will reconfigure the eye tracking algorithm.) A calibration verification process (active or passive) can then be performed to verify that the newly configured eye tracking algorithm is valid.

In another aspect, the calibration parameters are automatically changed in response to having identified that a different user is now in the seat 10 of the user console 2, where in that case a profile that is associated with the identified, different user is loaded into the eye tracking algorithm.

In another aspect, eye tracking verification can be added at any point in the workflow of the surgical robotic system, either actively or passively. This verification can be used to determine if the user in the seat 10 of the user console 2 has changed (without a logout process performed, or without a login process having been performed.)

In one aspect, the eye tracking process may be as follows. Referring to the block diagram of FIG. 3, the endoscope camera 115 sends its image data which captures a surgical tool 7 (as in FIG. 2 for example) to a video processor 153. The video processor 153 may detect the location of the action point 127 of the surgical tool 7, within the image data. Note the image data is also being shown on the view screen user display 15. FIG. 2 shows an example where the action point 127 happens to be roughly at the center of the display 15, but of course the action point 127 may be elsewhere on the view screen depending on the position of the tool 7. The video processor 153 may then code the detected location of the action point 127 into metadata of the image data. In one aspect, the location is coded as the pixel coordinates in the image frame in which the action point 127 appears. By appropriately aligning the endoscope camera 115 at a given position relative to the action point 127 the action point 127 will appear at a constant desired position (when the image data is displayed on the user display 15.) The position of the endoscope camera 115 relative to the action point 127 may then be held fixed. In another example, the endoscope camera 115 may be programmed to track the action point 127 of the surgical tool 7 (which may be moving.) The video processor 153 may have video analysis software that is programmed to detect the location of the action point 127, such as by machine learning.

Figure 3:
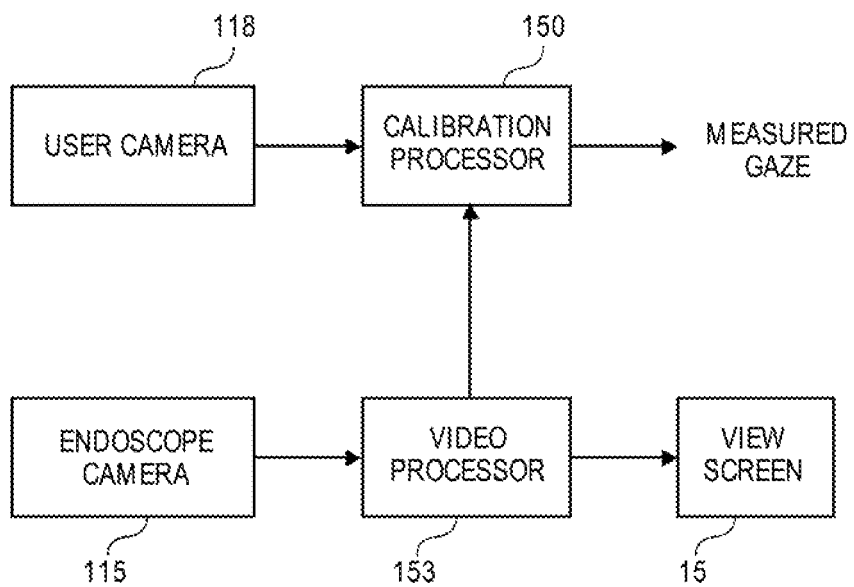
FIG. 3 illustrates a block diagram of a system for calibrating eye tracking for a surgical robotic system.

Still referring to FIG. 3, the video processor 153 outputs the image data it receives from the endoscope camera 115, to the user display 15 (View Screen), and also outputs the image data and its metadata to a calibration processor 150. The calibration processor 150 uses the received pixel coordinates of the action point 127 and its knowledge of how the image data maps to the format of the view screen, to determine a reference gaze point (an inferred specific location) on the display screen 15. The reference gaze point is a point on the view screen where the remote operator 9 would reasonably be expected to look while engaged with the surgical robotic system 1. The reference gaze point may be the coordinates on the user display 15 where the action point 127 appears (as the image data is being displayed.)

While the video processor 153 is outputting image data to the view screen user display 15, the user camera 118 which is aimed at the remote operator 9 is sending image data from its photographic sensor to the calibration processor 150. The calibration processor 150 is configured with eye tracking software that processes the image data from the user camera 118 to determine the measured gaze point 171 of the remote operator 9, as a point on the user display 15 (FIG. 2). The eye tracking software may use geometric characteristics of the eye of the remote operator 9, as input to a reference gaze geometry function, which allows the calibration processor 150 to determine the measured gaze point 171. The geometric characteristics of the eye of the remote operator 9 may include shapes, reflections, and refractions from different elements of the eye of the remote operator 9. The calibration processor 150 may thus determine the measured gaze point 171 of the remote operator 9 based on the geometric characteristics of the eye of the remote operator 9 that are input into the reference gaze geometry. These geometric characteristics of the eye may be part of the calibration parameters that can be set for each user (remote operator 9), by performing an eye tracking calibration process.

Referring now to FIG. 2, the calibration processor 150 then compares the measured gaze point 171 to the reference or inferred gaze point (e.g., the location of the action point 127 on the display screen 15.) If the difference between the measured gaze point 171 and the reference gaze point is outside the first threshold 174, then a mismatch has occurred, in response to which the calibration processor 150 adjusts the calibration parameters used by the tracking algorithm (to produce the measured gaze point 171.) In one aspect, the calibration parameters are adjusted until a new, measured gaze point 171 matches the reference gaze point in relation to the geometric characteristics of an eye of the remote operator 9. The calibration processor 150 may output calibration data, which may include all information relating to a current set of calibration parameters, such as whether the difference between the reference gaze point and the measured gaze point 171 falls within the first threshold 174, and a new, measured gaze point 171.

In one aspect, the reference gaze geometry function is determined by the geometric characteristics of the eye of the remote operator 9 when the remote operator 9 is looking at a known reference gaze point. The known reference gaze point may be an initial calibration point that was determined during a previous calibration procedure. For example, the remote operator 9 may be instructed to look at an initial calibration point on the display 15 (view screen). The photographic sensor may then send high frame rate images of the eye of the remote operator 9 to the calibration processor 150 while the remote operator 9 is looking at the calibration point. The calibration processor 150 may then determine the reference gaze geometry function based on the geometric characteristics of the eye of the remote operator 9 in relation to this initial calibration point.

In another aspect, the initial calibration point is or is based on an expected gaze point during a user action. For example, the remote operator 9 may be manipulating the UID 14 in order to position the surgical tool 7 within a surgical site during teleoperation (e.g., translate, rotate, or squeeze the UID, all of which are detected using a sensor subsystem that may include one or more sensor in the UID and possibly one or more sensors outside the UID, that are used for tracking the position and orientation of the UID 14 and on that basis controlling the surgical tool 7). In that situation, the expected gaze point is set to be the action point 127 of the particular surgical tool 7 that is being used on the patient. The action point 127 of that tool 7 may thus become the reference gaze point on the user display 15, without having to instruct the user to look at that point. In another aspect, the user action may include interfacing with the teleoperation software of the surgical robotic system. For example, the teleoperation software may instruct the remote operator 9 to select one of different options (e.g., graphical objects) within a graphical user interface (GUI) on the user display 15, such as during log in (but not as part of an eye tracking calibration routine.) When the remote operator 9 selects a particular GUI element that is being displayed on the user display 15, the known pixel coordinates of the selected GUI element may be used as the reference gaze point.

In one aspect, a plurality of calibration profiles may be stored, each having an associated reference gaze geometry function. Part of the process of an initial calibration could, in that case, include selection of one of those profiles. For example, when the remote operator 9 logs in to the teleoperation system, the profile associated with the logged in remote operator 9 who has been identified may automatically be loaded by the system, and therefore the associated reference gaze geometry function is then used by the eye tracking algorithm to track the user's gaze (generate the measured gaze.) In another example, the calibration parameters determined by an initial calibration process may be measured against a database containing a plurality of profiles to find a matching or corresponding profile; the attributes of that matching user profile contain a reference gaze geometry function that can then be selected for use by the eye tracking algorithm.

In another aspect, each profile may also contain one or more calibration parameters that depend on or are indicate of a condition of the remote operator 9. For example, there may be a parameter that refers to a scenario where the remote operator 9 is wearing glasses another parameter refers to a scenario for when the remote operator 9 is wearing contact lenses. A scenario for the remote operator 9 wearing glasses may have a different reference gaze geometry function than a scenario for the remote operator 9 wearing contact lenses.

In one aspect, when the difference between the measured gaze point 171 and the reference gaze point (e.g., action point 127) is outside a first threshold 174, the calibration processor may compare the difference against a second, further threshold 177 to determine if a new calibration profile is necessary. In one aspect, when the difference between the measured gaze point 171 and the reference gaze point is outside the second threshold 177, the calibration processor 150 may compare the geometric characteristics of the eye of the remote operator 9 associated with the measured gaze point 177 to the database of profiles. If the calibration processor 150 determines for example that there has been a change in the remote operator 9, the calibration processor may change the currently selected profile to one that is associated with the new remote operator 9. For example, if a remote operator 9 puts on glasses while operating, the difference between the measured gaze point 171 and the reference gaze point may now exceed the bounds of the second threshold 177. The calibration processor 150 may then select the reference gaze geometry from a different profile, to compute a new measured gaze point. The new measured gaze point may better match the reference gaze point, because the selected profile has the calibration parameters that have been tuned for instances where the remote operator 9 is wearing glasses. As a result, the calibration processor 150 will change the profile used by the eye tracking algorithm to the different profile that was selected (and that is indicative of the case where the remote operator 9 is wearing glasses.)

In another example, a first remote operator 9 may exit operation (leaves the user console 2) and then a second remote operator 9 may begin operation (enters the user console 2.) In that situation, the difference between the measured gaze point 171 (when the second remote operator has entered the user console 2) and the reference gaze point exceeds the bounds of the second threshold 177.

In that case, the calibration processor 150 may select another calibration profile (e.g., from a database of stored calibration profiles) that has a different gaze geometry function, and use it to calculate a new measured gaze point 171 (for the same image data.) If the new measured gaze point 171 is a closer or better match to the same reference gaze point, then the eye tracking algorithm is configured with the newly selected calibration profile. If none of the available calibration profiles result in a new measured gaze point 171 that is a close enough match to the same reference gaze point, then a new calibration profile is needed—in that case, an eye tracking calibration process needs to be performed upon the second remote operator 9 who is currently in the seat 10.

Figure 4:
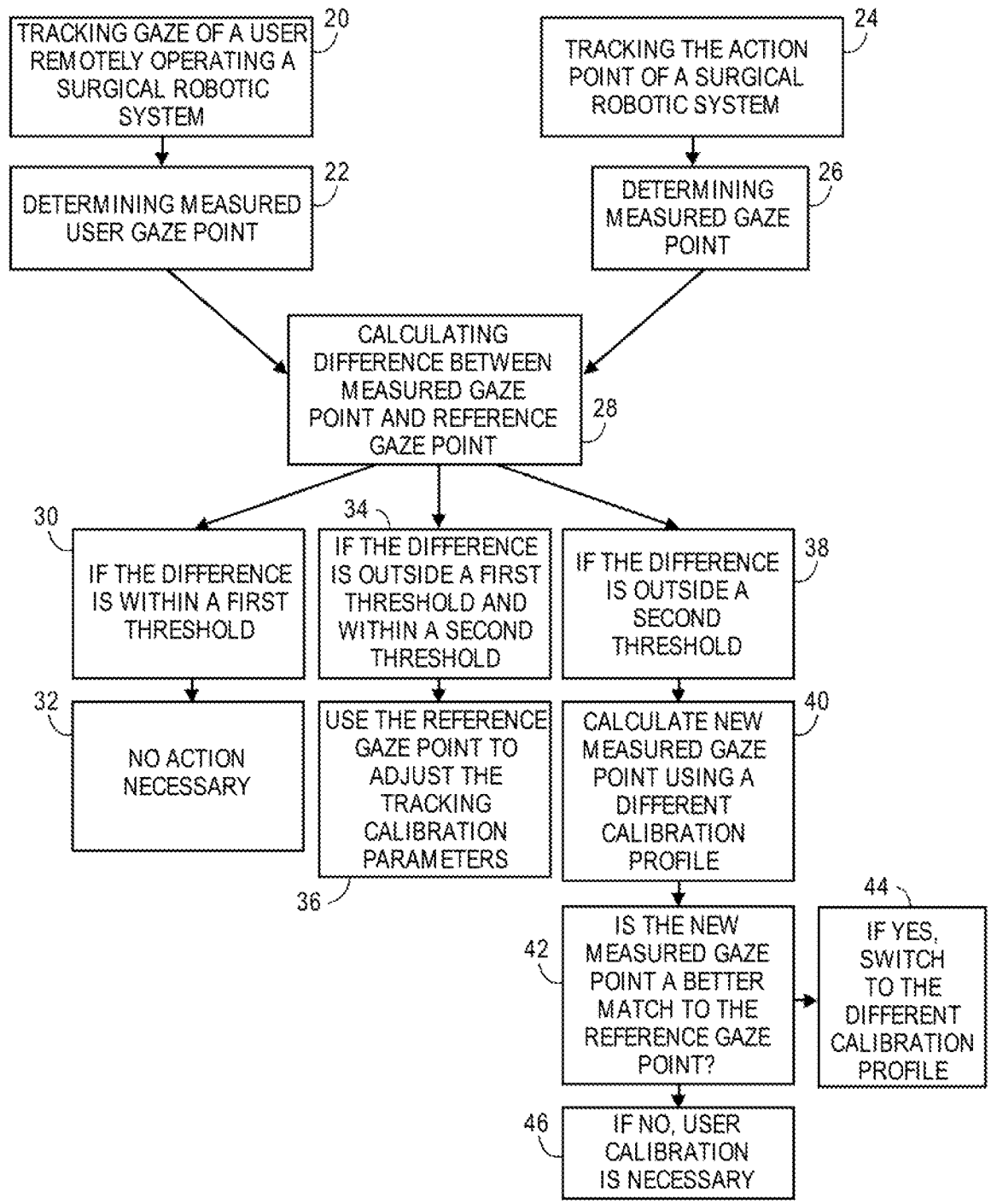
FIG. 4 depicts a flowchart of an example method for calibrating eye tracking for a surgical robotic system.

FIG. 4 is a flow chart demonstrating an example method performed by one or more programmed digital processors (generically referred to here as "a processor"), for adjusting an eye tracking process in a surgical robotic system. The gaze of a remote operator 9 that is remotely operating the surgical robotic system 1 as captured in the image data output by a user camera 118 is tracked, by the processor executing an eye tracking algorithm (block 20.) This means that a measured user gaze point is determined (block 22.) At the same time, since the remote operator 9 is engaged in teleoperation while sitting in the user console 2 and manipulating a UID 14, an endoscope camera 115 provides its video feed in which a surgical tool that is being remotely controlled by the system, according to manipulation of the UID 14 by the remote operator 9. This video feed is processed to track the action point of the surgical tool (block 24.) This means that a reference gaze point is determined (block 26), e.g., as a detected action point 127. The processor 153 encodes the coordinates of the action point 127 into the metadata of the video feed and sends the video feed with the encoded metadata to be processed in block 28, where using the metadata it calculates a difference between the measured gaze point 171 and the reference gaze point (e.g., action point 127.) If the difference falls within a first threshold 174 (block 30), then the user calibration is correct (no action is necessary in this process—block 32.) If the difference is not within the first threshold 174, then some form of adjustment to the calibration parameters used by eye tracking algorithm (in block 20) is required. This process may occur once, periodically, or continuously throughout teleoperation.

In one aspect, a second threshold 177 is defined which determines if the current calibration profile (whose gaze geometry function is being used in blocks 20-22 to determine the measured user gaze point) is incorrect. If the difference between the measured gaze point 171 and reference gaze point, measured from the user gaze image data and the action point 127 determined from the action point metadata, is within a second threshold 177 but outside a first threshold 174 (block 34), the current profile is deemed to be correct but adjustment of the calibration parameters is required. In one aspect, the processor in that case uses the reference gaze point to adjust the tracking calibration parameters (block 36) as was described above in more detail.

Returning to block 28, if the difference is outside the second threshold 177 (block 38), then the current profile is incorrect and needs to be changed—a different calibration profile is selected and used to compute a new measured gaze point (block 40.) This new measured gaze point is then tested, to determine if it is a better match to the reference gaze point (block 42.) If it is, then the eye tracking algorithm becomes reconfigured with the different profile (block 44), but if not then a full calibration, e.g., an active, conventional calibration process that instructs the user to look at target locations on the user display, is needed (block 46.)

In an aspect, a user profile may include a plurality of user cases. If the difference between the measured gaze point 171 and reference gaze point, measured from the user gaze image data and the action point 127 determined from the action point metadata, is outside a second threshold 177, the calibration processor 150 may determine if the user gaze better matches a different user case within the selected user profile. If the user gaze better matches a difference user case within the selected user profile, then the better matching user case is selected. If the user gaze does not better match a different user case within the selected profile, the selected user profile may need to be changed.

A method for eye tracking in a surgical robotic system may be as follows: tracking a gaze of a user facing a display of a user console of a surgical robotic system, while the user is using a user interface device (UID) at the user console to manipulate or actuate an end effector of a surgical tool within a surgical site that is inside a patient, the display showing an endoscopic view of the surgical site; detecting a user action to the UID including translating, rotating or squeezing; determining a position of the end effector on the display, as a reference gaze of the user at the time of detected user action; determining whether the tracked gaze of the user matches the reference gaze (as the position of the end effector at the time of detected user action); and in response to a determination of a mismatch, adjusting one or more calibration parameters used for the tracking of the user gaze.

While certain aspects have been described and shown in the accompanying drawings, it is to be understood that such are merely illustrative of and not restrictive on the broad invention, and that the invention is not limited to the specific constructions and arrangements shown and described, since various other modifications may occur to those of ordinary skill in the art. For example, while FIG. 1 depicts a single endoscope camera, it is also possible to have multiple endoscope cameras. The description is thus to be regarded as illustrative instead of limiting.

What is claimed is:

1. A method for eye tracking in a surgical robotic system, comprising:
    tracking a gaze of a user facing a display of a user console of a surgical robotic system while the user is using a user interface device (UID) thereby producing a measured gaze point of the user;
    detecting that the user is interacting with the UID thereby producing a detected user interaction;
    in response to the detected user interaction, determining an expected gaze point on the display of the user console at the time of the detected user interaction, as a reference gaze point of the user;
    in response to the detected user interaction, determining whether the measured gaze point at the time of the detected user interaction is within an acceptable threshold of the reference gaze point without prompting the user; and
    in response to determining the measured gaze point is within the acceptable threshold of the reference gaze point, continuing said tracking the gaze of the user without performing an eye tracking calibration.

2. The method of claim 1, wherein tracking the gaze of the user comprises utilizing an eye tracking sensor to calculate geometry and gaze point of an eye of the user.

3. The method of claim 1, wherein the detected user interaction comprises user login.

4. The method of claim 1, wherein the detected user interaction comprises interacting with graphical user interface, GUI, elements on the display.

5. The method of claim 1, wherein the display is showing an endoscopic view of a surgical site and the detected user interaction comprises manipulation of the UID by the user which causes actuation of an end effector within the surgical site, and wherein the expected gaze point is a determined position of the end effector on the display.

6. The method of claim 1, wherein said tracking the gaze of the user comprises performing an eye tracking algorithm that uses a plurality of parameters, and the expected gaze point comprises coordinates on the display where an action point appears at the time of the detected user interaction, and wherein in response to determining the measured gaze point is within the acceptable threshold, continuing said tracking without adjusting the plurality of parameters.

7. The method of claim 6, wherein in response to determining that the measured gaze point is within a first acceptable threshold of the reference gaze point, one or more of the plurality of parameters are adjusted until the tracking produces a measured gaze point that is within the acceptable threshold of the reference gaze point.

8. The method of claim 7 wherein in response to determining that the measured gaze point is outside the first acceptable threshold but inside a second acceptable threshold of the reference gaze point, the method further comprises:

selecting a stored profile from a database of stored profiles, wherein the stored profile contains a plurality of parameters to be used by an eye tracking algorithm; and re-configuring the eye tracking algorithm in accordance with the plurality of parameters in the selected stored profile.

9. The method of claim 8 further comprising one of:

a) in response to determining that the measured gaze point as produced by the reconfigured eye tracking algorithm is a better match to the reference gaze point, continuing the tracking in accordance with the selected stored profile; or b) in response to determining that the measured gaze point as produced by the reconfigured eye tracking algorithm is not a better match to the reference gaze point, performing an eye tracking calibration process to create a new profile.

10. A method for calibrating eye tracking in a surgical robotic system, comprising:

generating a measured gaze by a process for tracking a gaze of a user facing a display of a user console of a surgical robotic system while the user is using a user interface device (UID);

detecting a user action to the UID;

in response to detecting the user action to the UID, determining an expected gaze position on the display of the user console at the time of detecting the user action, as a reference gaze of the user;

in response to detecting the user action to the UID, determining whether a mismatch has occurred without prompting the user, wherein a mismatch has occurred if the measured gaze of the user at the time of detecting the user action is outside a first threshold and within a second threshold of the reference gaze; and in response to a determination of a mismatch, adjusting one or more parameters used by the process for tracking the gaze until the process produces the reference gaze.

11. The method of claim 10, further comprising determining if the difference between the reference gaze and the measured gaze is outside the second threshold, and if so then selecting a different profile to be used by the process for tracking the gaze to generate a new measured gaze, and then determining if the new measured gaze is a closer match to the reference gaze, and if so, selecting the different profile for use by the process.

12. The method of claim 10, further comprising determining if the difference between the reference gaze and the measured gaze is outside the second threshold, and if so then selecting a different profile to be used by the process for tracking the gaze to generate a new measured gaze, and then determining if the new measured gaze is a closer match to the reference gaze, and if not, performing an eye tracking calibration method to produce a new profile.

13. The method of claim 10 wherein determining an expected gaze position on the display of the user console as a reference gaze of the user at the time of detected user action comprises:

identifying an on-screen position of a visual element that is not generated as part of an eye tracking calibration process;

determining how the measured gaze changes over time, before and after the visual element appears on screen; and determining vicinity of the measured gaze to the visual element on screen.

14. The method of claim 13 wherein the detected user action to the UID is interaction of the user with the visual element being a mouse cursor or a dialog box.

15. A device for calibrating eye tracking in a surgical robotic system, comprising:

a camera aimed at a user seat, wherein the user seat is facing a user display of a user console of a surgical robotic system having a user interface device (UID) that is to be manipulated by a user;

a memory having instructions stored therein; and one or more processors to execute the instructions to detect a user action by a user to the user console or to the UID, based on the detected user action, determine an expected gaze position on the user display of the user console at the time of detected user action, as a reference gaze of the user, track a gaze of the user using an eye tracking algorithm that receives as input image data from the camera and uses a plurality of eye tracking calibration parameters, determine whether the tracked gaze of the user at the time of detected user action is within an acceptable threshold of the reference gaze, and continuing to track the gaze of the user without changing the eye tracking calibration parameters, in response to a determination that the tracked gaze is within the acceptable threshold.

16. The device of claim 15, wherein the detected user action is user login.

17. The device of claim 15, wherein the detected user action is interaction with GUI elements on the user display.

18. The device of claim 15, wherein the user display is showing an endoscopic view of a surgical site and the detected user interaction comprises manipulation of the UID by the user, wherein the manipulation of the UID causes actuation of an end effector within the surgical site, and wherein the expected gaze position is a determined position of the end effector on the user display.

19. The device of claim 18 wherein the processor is to execute the instructions to determine the position of the end effector on the user display by:

determining a joint state of a robotic arm to which the end effector is attached and is being controlled in accordance with manipulation by the user of the UID;

transforming the joint state of the robotic arm to endoscope image frame domain;

transforming from the endoscope image frame domain to user display frame domain.

* * * * *